Figure 1:
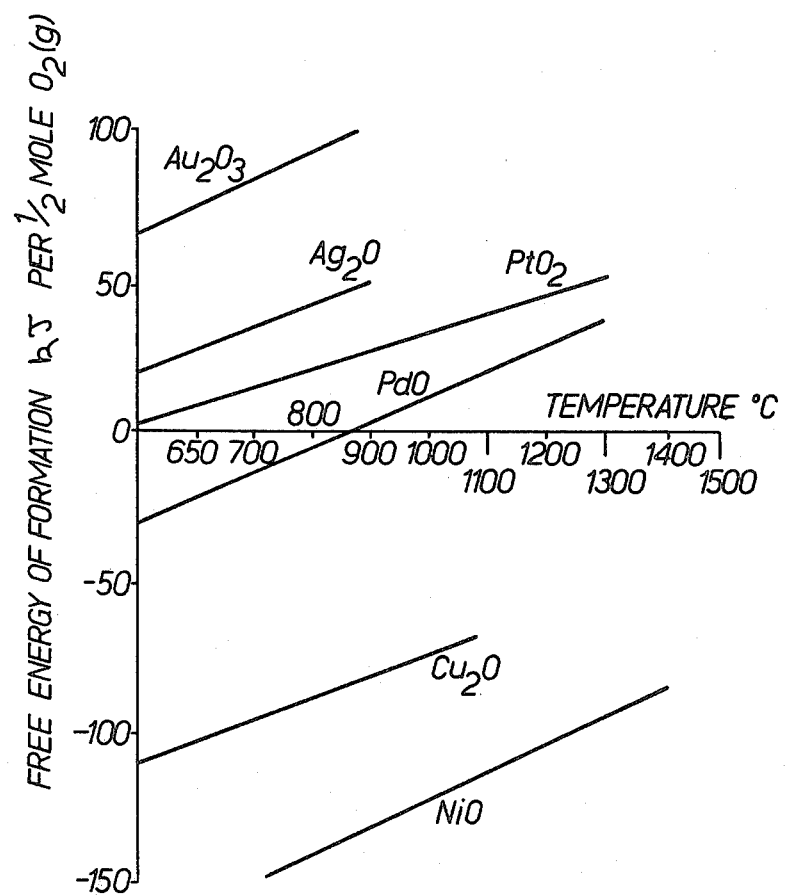

United States Patent [19]

de Bruin et al.

[11] 4,384,934

[45] May 24, 1983

[54] MEANS FOR DETERMINING THE PARTIAL PRESSURE OF OXYGEN IN AN ATMOSPHERE

[75] Inventors: Henderikus J. de Bruin, Bellevue Heights; Sukhvinder P. S. Badwal, Ingle Farm, both of Australia

[73] Assignee: The Flinders University of South Australia, Australia

[21] Appl. No.: 42,229

[22] Filed: May 24, 1979

[30] Foreign Application Priority Data

May 31, 1978 [AU] Australia .................. PD4563
Nov. 17, 1978 [AU] Australia .................. PD6823

[51] Int. Cl.³ ........................................ G01N 27/58
[52] U.S. Cl. ............................ 204/406; 324/65 R; 324/441; 324/464; 324/71.1; 204/425; 204/426
[58] Field of Search ................ 204/195 S, 1 S; 324/441, 464, 468, 65 R, 71 R; 73/23; 422/98

[56] References Cited

U.S. PATENT DOCUMENTS

| | | | |
|---|---|---|---|
| 3,654,112 | 4/1972 | Beekmans et al. | 204/195 S |
| 3,915,135 | 10/1975 | Kushida et al. | 204/195 S X |
| 4,129,099 | 12/1978 | Howarth | 204/195 S |
| 4,134,818 | 1/1979 | Pebler et al. | 204/195 S |
| 4,190,499 | 2/1980 | Pebler | 204/1 T |

*Primary Examiner*—G. L. Kaplan
*Attorney, Agent, or Firm*—Cushman, Darby & Cushman

[57] ABSTRACT

A method of measuring the oxygen partial pressure in an atmosphere in which a temperature $T_c$ at which the free energy of formation of an oxide of a metal such as palladium in contact with the atmosphere is determined to provide a measure of the partial pressure of oxygen. Apparatus for use in the method comprises an electrolytic cell including an electrode of the said metal and an electrolyte such as yttria stabilized zirconia having ionic oxygen mobility.

9 Claims, 8 Drawing Figures

MEANS FOR DETERMINING THE PARTIAL PRESSURE OF OXYGEN IN AN ATMOSPHERE

This invention relates to the measurement of oxygen partial pressures in an atmosphere and to devices involving such measurements.

At present there are three methods commonly used for the measurement of oxygen partial pressures in industrial and laboratory atmospheres and these are:

1. Offline chemical analysis. In this procedure, a sample of flue gas or ambient atmosphere is withdrawn and analyzed, most commonly by gas chromatography. The method is labour-intensive, requires expensive laboratory facilities and does not provide results in time to be practically useful in monitoring transient conditions.
2. The oxygen differential pressure probe based on a galvanic cell of the general type:

(Reference oxygen atmosphere), platinum—stabilized zirconia-platinum, (unknown oxygen atmosphere)

At a given and constant temperature, the e.m.f. of such a cell is logarithmically related to the ratio of the oxygen partial pressure in a reference atmosphere and the oxygen partial pressure in the unknown ambient atmosphere. This is currently the most widely-used type of oxygen probe. It has, however, the disadvantage that it needs a reference atmosphere at the same temperature as that of the unknown atmosphere. This complicates the construction of the probe by requiring hermetic seals between the reference and unknown atmospheres. This can be a serious disadvantage in often hostile industrial environments. Moreover, the probes are fragile and particularly sensitive to thermal stresses, and it has been found that the accuracy of the device decreases with use due to absorption and diffusion of impurities from the ambient atmosphere.

3. The cobalt oxide wire probe, in which the conductance of the wire is measured at 1000° C. The non-stoichiometric cobalt oxide absorbs oxygen in dependence upon its partial pressure in the ambient atmosphere. This increases the conductivity of the wire. This method is used mainly under laboratory conditions when the partial pressure of oxygen remains constant over long periods (several days). The response depends upon the attainment of equilibrium conditions, which is rarely ever the case in an industrial environment.

The general object of the present invention is, accordingly, to provide a method and means for the measurement of oxygen partial pressures which provide improvements in the art as present practised, namely there is no need for either a reference atmosphere or a reference electrode.

According to the present invention there is provided a method of determining the partial pressure of oxygen in an atmosphere, in which a temperature $T_c$ at which the free energy of formation of an oxide of a metal in contact with the atmosphere becomes zero is determined to provide a measure of the partial pressure of oxygen in the said atmosphere.

According to the present invention there is also provided an electrochemical sensing device, hereinafter referred to as a sensor, for determining the partial pressure of oxygen in an atmosphere, the sensor comprising an electrolytic cell adapted to be located in said atmosphere and means having a temperature-dependent property which enables the temperature of the sensor to be determined when the sensor is located in said atmosphere, the electrolytic cell including an electrolyte having ionic oxygen mobility and an electrode composed of a metal characterized in that the free energy of formation of an oxide of the metal becomes zero at a temperature $T_c$ within the operating temperature range of the cell.

In use, the sensor is associated with means for determining the temperature at which the free energy of formation of said oxide becomes zero to thereby determine the partial pressure of oxygen in the atmosphere.

Figure 2:
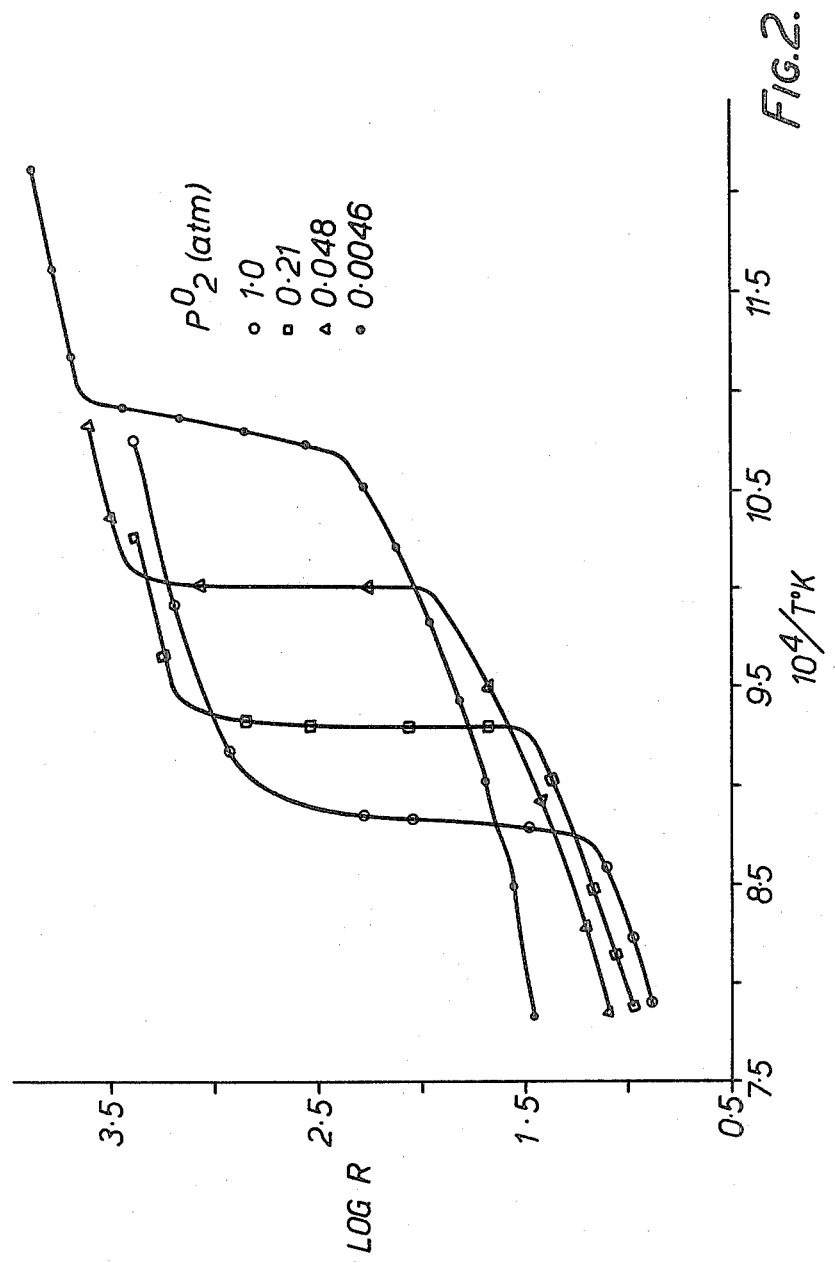
Figure 3:
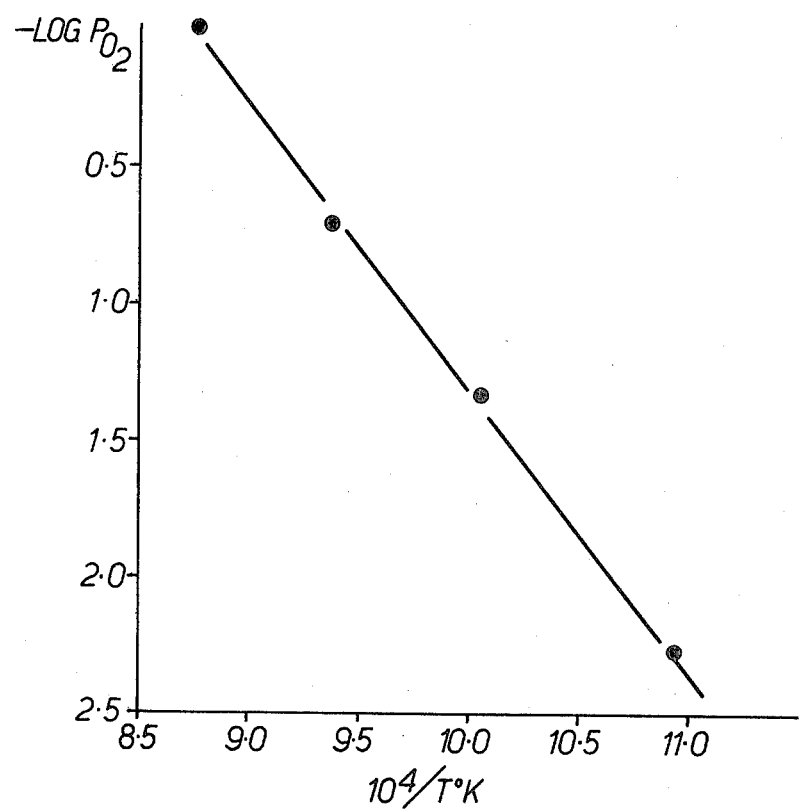
Figure 4:
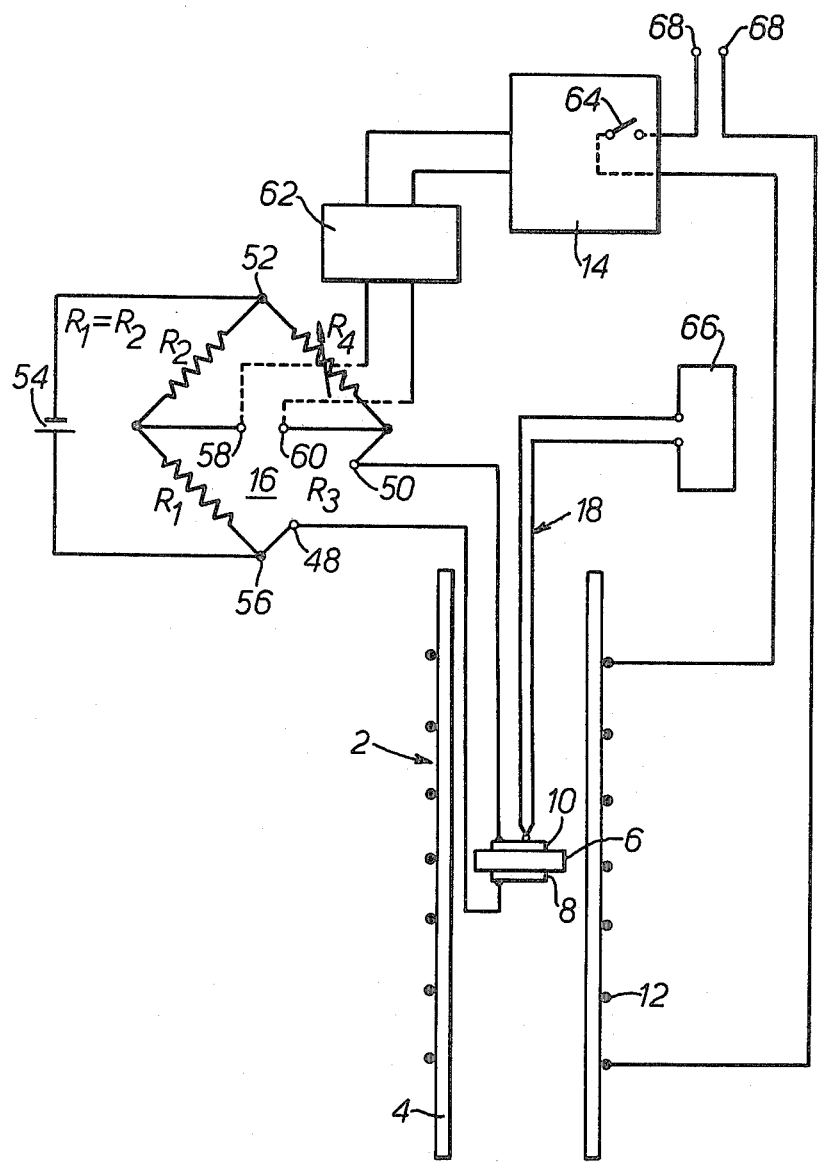
Figure 5:
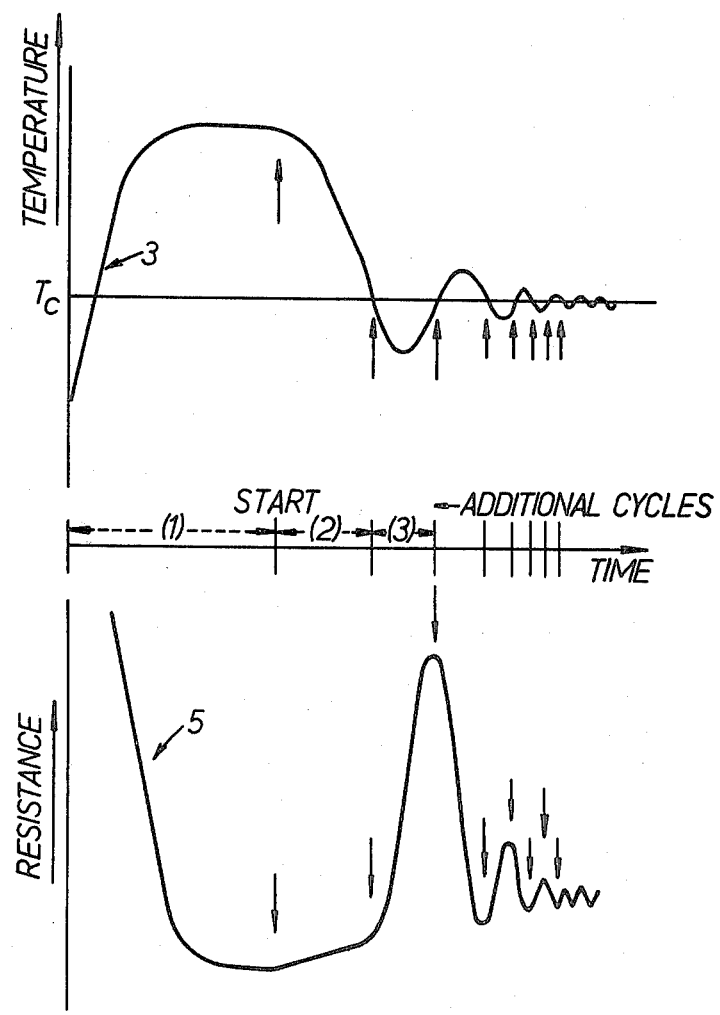
Figure 6:
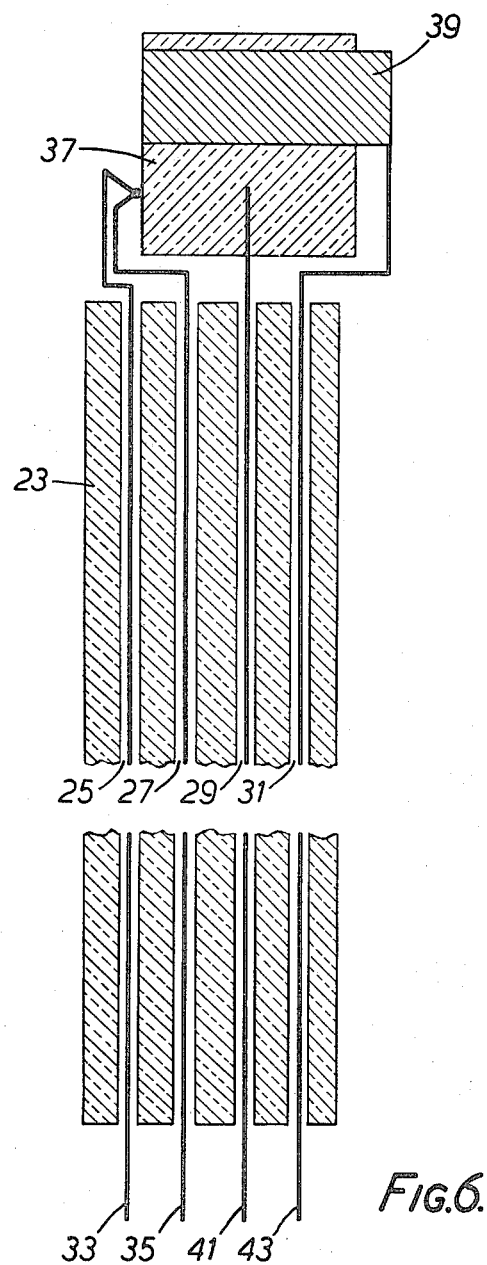
Figure 7:
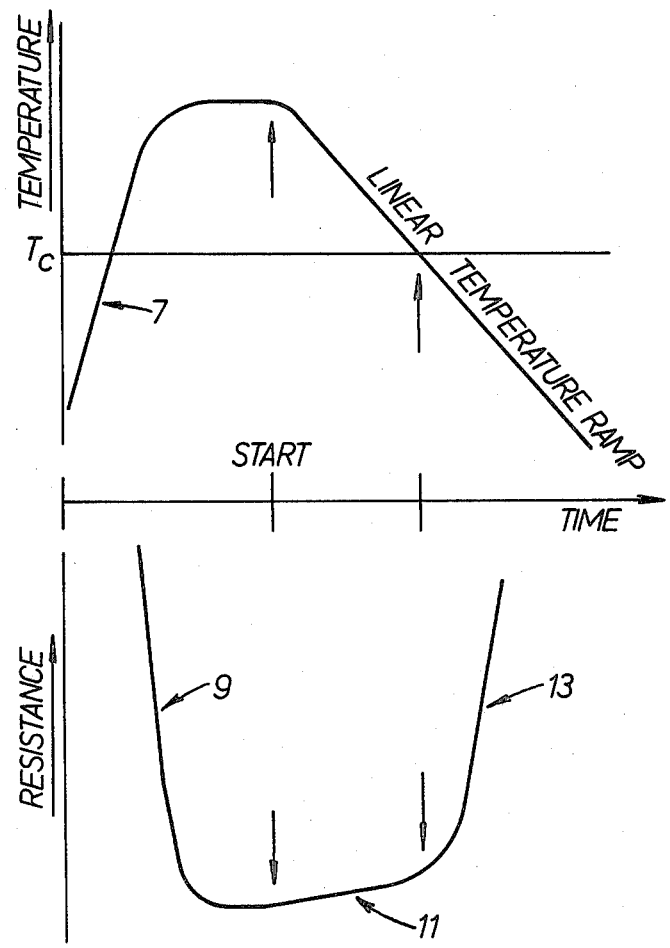
Figure 8:
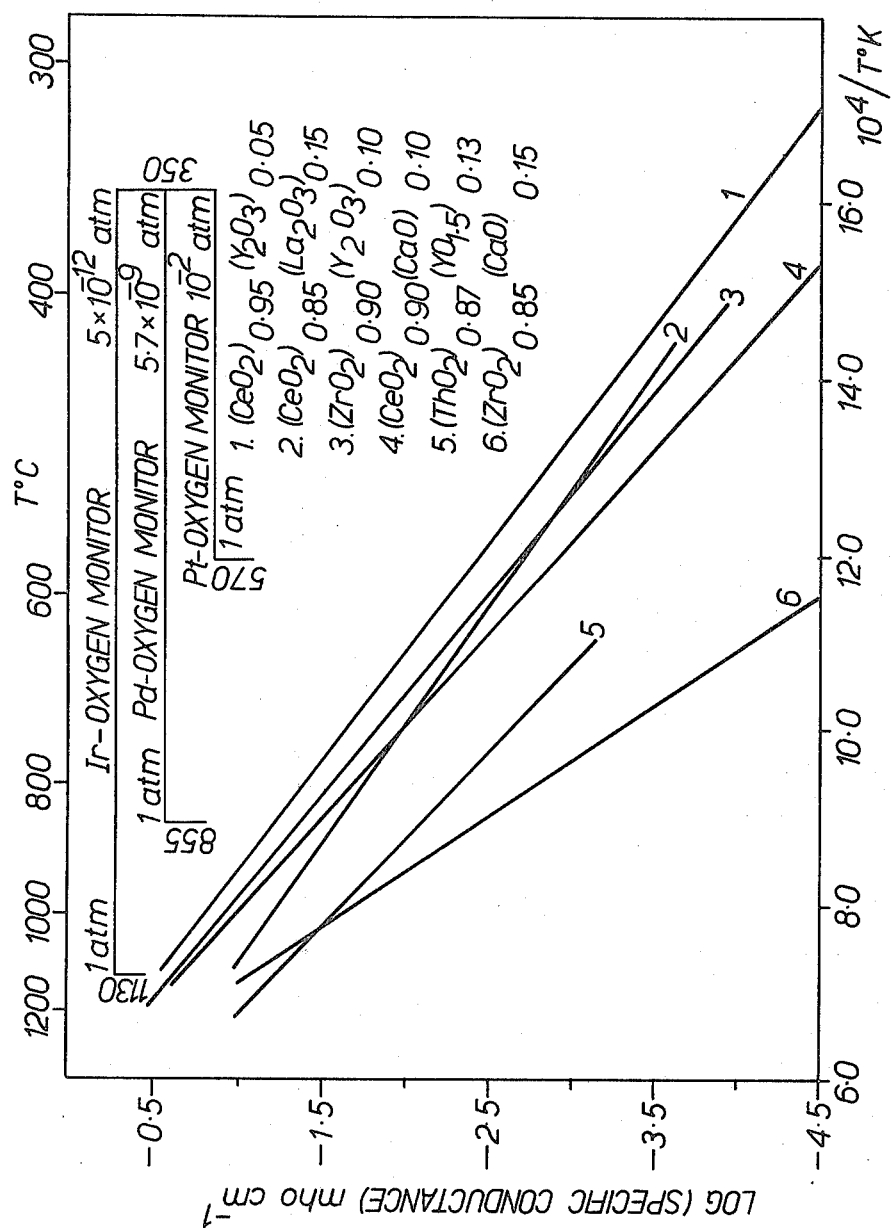

The invention will be further described with reference to the accompanying drawings, in which:

FIG. 1 is a graph illustrating the variation in the free energy of formation of various metal oxides in the temperature range 500° to 1400° C., FIG. 2 is a graph illustrating the variation of resistance with the inverse of the absolute temperature of a palladium/yttria stabilized zirconia/palladium cell heated in environments containing various partial pressures of oxygen, FIG. 3 is a graph derived from FIG. 2, which illustrates the variation of the partial pressure of oxygen with temperature, FIG. 4 is a schematic view of apparatus, including one form of sensor in accordance with the present invention, FIG. 5 is a graph illustrating one example of the method of the present invention, FIG. 6 is a schematic view of another form of sensor in accordance with the present invention, FIG. 7 is a graph illustrating another example of the method of the present invention, and FIG. 8 is a diagram illustrating the properties of some metals and electrolytes suitable for use in the present invention.

In FIG. 1, the variation in free energy of formation of a number of metal oxides with temperature within a temperature range of 500° C.–1400° C. is shown. Within this temperature range, the only one of the various metal oxides to exhibit both a positive free energy of formation and a negative free energy of formation is palladium oxide, and the temperature at which the free energy of formation of palladium oxide is zero is 868±5° C. The results illustrated in FIG. 1 were compiled from thermodynamic data obtainable in the International Critical Tables from which oxygen partial pressures can be calculated. For example, for palladium:

$$\log P_{O_2} = [(-11,306 \pm 397)/T] + (9.90 \pm 0.38) \text{ (with T in Kelvin)}.$$

FIG. 2 is a graph illustrating the variation of resistance versus the inverse of the absolute temperature for a cell having both electrodes of palladium and an electrolyte composed of 10 m% yttria stabilized zirconia in atmospheres having partial pressures of oxygen ranging from 0.0046 atmosphere to 1.0 atmosphere. This graph shows that for each atmosphere, as the temperature approaches the temperature $T_c$ at which the free energy of formation of palladium oxide becomes zero (hereinafter referred to as the critical transition temperature), the rate of increase of the electrical conductivity of the cell with temperature sharply increases. Further, the graph illustrates that the critical transition temperature is dependent on the partial pressure of oxygen in the environment being tested.

FIG. 3 is a graph derived from FIG. 2, which illustrates the straight-line variation of oxygen partial pressure with $1/T_c$.

This confirms that $T_c$ varies with the partial pressure of oxygen in the environment in which the metal is located, and that a functional relationship can be derived uniquely relating the partial pressure of oxygen and $T_c$. Further there is a high rate of change of the electrical conductivity across the metal/electrolyte interface with temperature at $T_c$, and it is thus possible to calibrate apparatus to measure the partial pressure of oxygen in an environment being tested, by measuring $T_c$.

One form of sensor based on the principle of the present invention is shown in FIG. 4. In the sensor 2, an electrolyte in the form of a disc 6 of yttria stabilized zirconia or other suitable material is enclosed in a tubular element 4 of alumina. On one side of the electrolyte, a working electrode 8 composed of palladium is attached. The palladium may be in the form of a thin foil which is welded to the electrolyte, it may be in the form of a paste composed of sub-micron palladium powder in a suitable organic base, or it may be applied by an ion sputtering or vacuum evaporation technique. On the other side of the electrolyte, a counter-electrode 10 composed of platinum is attached. Similarly, the platinum may be in the form of a foil which is welded to the electrolyte, it may be applied in the form of a paste, or it may be applied by an ion sputtering or vacuum evaporation technique.

Suitable heating means are provided to heat the region contained within the tubular element 4. In the illustrated embodiment, the heating means are shown as comprising a plurality of electrical windings 12 wrapped around the outer surface of the tubular element and connected to a mains power supply 68.

Working electrode 8 is connected to one resistor terminal 48 of a resistor $R_3$ of a wheatstone bridge 16, and counter-electrode 10 is connected to the other resistor terminal 50 of resistor $R_3$. The wheatstone bridge further comprises resistors $R_1$ and $R_2$ which are set at constant values, and a variable resistor $R_4$. A power source 54 is connected across one pair of opposed bridge terminals 52 and 56.

A furnace triggering means is connected across the other pair of opposed bridge terminals 58 and 60. The furnace triggering means comprises an optically isolated solid state relay 14 and an amplifier 62. The optically isolated solid state relay 14 includes a switch 64 which is connected to the circuit supplying power from the mains 68 to the electrical windings 12. In use, an imbalance in the bridge circuit, which is amplified by the amplifier 62, will result in the switch 64 changing from either an open position or a closed position, and thus either connecting or disconnecting the mains supply 68 to or from the electrical windings 12.

One end of each lead of a thermocouple 18 is connected to counter-electrode 10. The opposite end of each lead of the thermocouple 18 is connected to a potentiometer 66, which measures the thermo-potential of the thermocouple 18 and is calibrated in units of oxygen partial pressures according to known relationships.

In most practical applications of the present invention it is not necessary to measure partial pressures of oxygen in excess of one atmosphere. Thus, as will be evident from FIG. 1, which illustrates test results compiled for oxygen partial pressures in the ambient atmosphere of unity, the maximum operating temperature of the apparatus need normally not be much in excess of $868 \pm 5°$ C.

FIG. 5 illustrates one example, which will hereinafter be referred to as the temperature cycling technique, of the method of determining the partial pressure of oxygen in an atmosphere according to the present invention. It is the recommended method for continuously monitoring oxygen partial pressures as opposed to one-off measurements.

In this figure, the upper curve 3 shows the variation of temperature with respect to time of a sensor having a palladium electrode in the atmosphere being tested. The lower curve 5 shows the corresponding variation in the cell resistance with respect to time. The temperature cycling technique comprises the steps of (1) heating the atmosphere to a temperature in excess of $T_c$, (2) cooling the atmosphere whilst continuously measuring the electrical resistance of the cell until a first temperature is reached at which a substantial increase in the resistance of the cell is detected, (3) reheating said atmosphere whilst continuously measuring the resistance of the cell until a second temperature is reached at which a substantial decrease in resistance is detected, alternately cooling and reheating the atmosphere as in steps (2) and (3) respectively until the temperatures at which a substantial change in the resistance of the cell is detected, converge to a substantially constant temperature, thereby determining $T_c$ and providing a measurement of the partial pressure of oxygen in the atmosphere.

The form of the sensor as described in the foregoing and in FIG. 4 may be used to carry out the temperature cycling technique. Before describing the use of the method it should be noted that for oxygen partial pressures in an ambient atmosphere of unity or less, the resistance of the cell which is continually monitored by the wheatstone bridge circuit 16, will be low. The variable resistance $R_4$ in the bridge is set to a value intermediate between the low and high resistance modes for the particular cell. The high resistance mode corresponds to the presence of metal oxide at the metal/electrolyte interface, the low resistance mode to the absence of metal oxide. For the cell used to obtain the data in FIG. 2 for example, $R_4$ should be set between the limits 200 and 320 ohms. In use, the heating means are switched on and the cell comprising the electrode 8, the electrolyte 6 and the counter-electrode 10 reaches a termperature above $T_c$. The heating means will automatically switch off and the cell temperature will drop until the wheatstone bridge detects a substantial increase in resistance in excess of $R_4$. This will cause an imbalance in the wheatstone bridge, which consequently triggers a reversal of the cooling cycle and the heating means switches on automatically. The heating means then remains on until the temperature of the cell approaches the critical transition temperature at which time the wheatstone bridge senses a decrease in resistance below the set value of $R_4$. This again causes an imbalance in the bridge and brings about a further reversal of the heating cycle. After several such reversals, the temperature settles at the $T_c$ and the thermocouple 18, which monitors the temperature of the cell, provides the value of this temperature. The output signal from the thermocouple is calibrated on a millivolt meter directly in pressure units of oxygen in the ambient atmosphere, thus providing a value for the partial pressure of the oxygen in the environment being tested.

It has been found that the critical transition temperature range over which palladium is useful is between 350° C. and 868±5° C., which corresponds to oxygen partial pressures between $5.6 \times 10^{-9}$ and 1.0 atmospheres respectively in a logarithmic relationship.

A second form of sensor based on the principle of the present invention is shown in FIG. 6.

The form of sensor illustrated in FIG. 6 comprises a cylindrical rod 23 of alumina, the rod having four holes 25, 27, 29 and 31 extending lengthwise therethrough. The length and diameter of the rod illustrated are of the order of 15 mm and 5 mm respectively. Adjacent one end of rod 23 is positioned a block 37 of yttria stabilized zirconia. Around a portion of the outer surface of block 37 is secured a working electrode 39 in the form of a thin layer of palladium. Thermo-couple leads 33, 35 extend through the holes 25 and 27 respectively and are connected to block 37. Platinum cell leads 41, 43 extend through the holes 29 and 31 respectively. One end of the cell lead 41 is connected to block 37, and one end of lead 43 is connected to palladium working electrode 39.

As in the case of the first form of sensor described above, a wheatstone bridge or equivalent resistance measuring device and heating means are provided, and the other end of each of the platinum cell leads 41 and 43 is connected to the wheatstone bridge or other resistance measuring device.

In many instances it is preferred to use the second form of sensor according to the present invention, for the following reasons:
1. It may be of such small dimensions as to render it particularly suitable and convenient for combustion control applications in the automotive industry.
2. It can be constructed of relatively cheap materials, leading to a substantial reduction in unit price in comparison with devices at present in use. This makes replacement acceptable in preference to repair. This is important because of the effects of the hostile environments (high temperature, rapid erosion, etc.) where oxygen probes are commonly used.
3. It is particularly suitable for use in large scale automated manufacturing processes, thus making oxygen analysis feasible in many environmental pollution control situations.
4. It has a rapid response to temperature changes and is thus less subject to damage through thermal stresses.
5. It requires very low power heating for operation. Thus, for example, the power required for a car cigarette lighter is adequate to raise the temperature of the sensor to 900° C. in 1–2 minutes (∼50–100 watt).

The second form of sensor may be used to carry out the temperature cycling technique. The second form of sensor may also be used to carry out another example of the method of the present invention, which will hereinafter be referred to as the temperature ramping technique. This technique will now be described with reference to FIG. 7.

In FIG. 7, curve 7 shows the variation of temperature with respect to time of a sensor in an atmosphere being tested, and curve 9 shows the variation of resistance with respect to time of a sensor in the atmosphere. The graph shows that the resistance versus time curve 9 for a sensor in an atmosphere which is being cooled at a constant rate is characterized by two distinct regions 11 and 13. In region 11, between 900° C. and $T_c$, the change in resistance with respect to time of the sensor in the atmosphere being tested is substantially linear. In region 13, for temperatures below $T_c$, the change in resistance with respect to time of the sensor in the atmosphere being tested is substantially exponential. Accordingly, the temperature ramping technique is based on the concept of determining $T_c$ by ascertaining the temperature at which the slope of the resistance versus time curve 9 for a sensor in the atmosphere being tested which is being cooled at a constant rate, increases from slow and linear to substantial and exponential. It should be appreciated that although FIG. 7 illustrates a procedure in which the temperature is reduced at a constant rate from a temperature in excess of $T_c$, the procedure may readily be modified by heating the atmosphere at a constant rate from a temperature below $T_c$ towards $T_c$.

The above described temperature ramping technique may also be used in conjunction with the first form of sensor of the present invention. It will of course be readily appreciated by those skilled in the art that in that case it would not be necessary to use the furnace triggering circuitry.

In many instances it is preferred to use the temperature ramping technique of the present invention, particularly where one-off measurements are adequate in contrast to the monitoring mode, previously described, under the temperature cycling technique, for the following reasons:
1. The response rate depends only on the thermal inertia of the furnace.
2. Sensors constructed for use with the temperature ramping technique may be of much simpler design insofar as the electronic printed circuitry is concerned and there is no need to use power switching devices.
3. The life expectancy of sensors constructed for use with the temperature ramping technique will be increased as the time at high operating temperatures will be substantially reduced.
4. The time required to determine $T_c$ is substantially shorter than that needed when using the temperature cycling technique since it is necessary to cool or heat the atmosphere only once from a temperature above or below $T_c$.

In use of the second form of sensor according to the present invention to carry out the temperature ramping technique, the sensor is heated to a temperature in excess of 868±5° C.; and control-cooled at a constant linear rate. The wheatstone bridge continuously monitors the resistance of the cell during cooling. When the temperature reaches $T_c$ the wheatstone bridge detects an imbalance which is caused by the sudden change in resistance with time of the cell at $T_c$ (as is illustrated in FIG. 7). In a similar manner to that previously described in relation to the use of the first form of sensor to carry out the temperature cycling technique, the output signal from the thermocouple is calibrated on a millivolt meter directly in pressure units of oxygen in the ambient atmosphere, thus providing a value for the partial pressure of the oxygen in the environment being tested.

Although the embodiments of the present invention have been described above using a palladium working electrode, palladium is not the only material that could be used. For instance, iridium, platinum, ruthenium or nickel could take the place of palladium. Alloys of these metals with other noble metals may also be used, for example, palladium-gold alloys which can be easily deposited on electrolyte surfaces by ion sputtering techniques. It has been found that for iridium and platinum, the critical transition temperature at one atmosphere partial pressure is 1130° C. and 570° C. respectively.

In general, the choice of material for the working electrode is governed by the properties of the material in the operating temperature range of the device, the properties being such that within the operating range of the device the material has a critical transition temperature at which the free energy of formation of the metal oxide becomes zero.

The choice of the electrolyte material does not affect the principle of measurement of the cell, but only its useful oxygen partial pressure range. However, the electrolyte is preferably one with substantial ionic oxygen mobility, a property which is often found in the oxides with fluorite related structures. It has been found that yttria stabilized zirconia is useful to temperatures as low as 500° C., corresponding to an oxygen partial pressure of $2 \times 10^{-5}$ atmosphere, if a palladium working electrode is used. This is adequate for most industrial applications of the sensor. The basic limitation on the choice of the electrolyte is its conductance, which at the temperature of operation must not be less than the electrode interfacial conductance.

For very low oxygen partial pressures, a more highly conducting solid electrolyte needs to be used, and one example that has been found to be successful is yttria stabilized ceria, which has a useful temperature range of between 350° C. and $868 \pm 5°$ C., which is equivalent to an interval of partial pressures of between $5.6 \times 10^{-9}$ and one atmosphere, if a palladium working electrode is used.

The possible choices of some of the metals and electrolyte are summarized in FIG. 8. This diagram is not exhaustive. Thus other electrolytes with high ionic oxygen mobility are available, while other metals in Group VIII and Group Ib of the Mendeleev periodic classification are suitable for use as working electrodes. FIG. 8 refers specifically to the metals iridium, palladium and platinum. The range of oxygen partial pressures defined by the line for each metal in the upper part of the diagram is set by the transition temperature shown at the left hand end of each line and an arbitrary lower temperature of 350° C. indicated on the right, below which the electrolytes shown become insufficiently conductive.

In place of platinum the counter-electrode may be gold, silver or any other suitable metal.

If the counter-electrode metal is identical to the working electrode metal an increase in sensitivity is obtained.

It will be apparent to those skilled in the art that the present invention has a wide range of application. It could, for instance find application in monitoring oxygen levels in motor vehicle emissions and in the control of ambient atmospheres in the metallurgical, chemical and power industries.

We claim:

1. Apparatus for determining the partial pressure of oxygen in an atmosphere, comprising a cell having an active electrode which is in use exposed to said atmosphere and a counter electrode separated from the active electrode by a solid electrolyte material having ionic oxygen mobility, said active electrode being composed of a metal exhibiting both positive and negative free energy of formation of an oxide of said metal, said cell operating in the so-called high resistance mode when oxide is present at the active electrode/electrolyte interface and in the so-called low resistance mode when oxide is absent at the active electrode/electrolyte interface, the temperature $T_c$ at which the free energy of formation of said oxide becomes zero being related to the partial pressure of the oxygen in said atmosphere, detection means responsive to changes in the resistance of said cell resulting from the oxidation/reduction of said active electrode caused by temperature changes in said atmosphere to detect a situation in which the free energy of formation of said oxide becomes zero, heating means operable to control the temperature of said cell, heating control means responsive to said detection means and temperature responsive means responsive when said detection means detects said situation to generate a signal representative of $T_c$, wherein said detection means comprises a wheatstone bridge in which one arm is said cell and another arm of said wheatstone bridge has a resistance intermediate the low and high resistance modes of the cell whereby said heating control means being controlled by said wheatstone bridge whereby said heating means is inoperative when said cell is in the low resistance mode and operative when said cell is in the high resistance mode thereby to attain a steady state condition at which the temperature of the cell is substantially $T_c$.

2. An apparatus according to claim 1, wherein said temperature responsive means comprises a thermo-couple connected to said cell, said thermo-couple being coupled to display means calibrated to convert the signal from said thermo-couple into a direct reading of the partial pressure of oxygen in said atmosphere.

3. An apparatus according to claim 1 or claim 2, wherein said active electrode is composed of palladium.

4. An apparatus according to claim 1 or claim 2, wherein said active electrode is composed of iridium, platinum, ruthenium, or nickel or alloys thereof.

5. Apparatus for determining the partial pressure of oxygen in an atmosphere, comprising a cell having an active electrode which is in use exposed to said atmosphere and a counter electrode separated from the active electrode by a solid electrolyte material having ionic oxygen mobility, said active electrode being composed of a metal exhibiting both positive and negative free energy of formation of an oxide of said metal, said cell operating in the so-called high resistance mode when oxide is present at the active electrode/electrolyte interface and in the so-called low resistance mode when oxide is absent at the active electrode/electrolyte interface, the temperature $T_c$ at which the free energy of formation of said oxide becomes zero being related to the partial pressure of the oxygen in said atmosphere, detection means responsive to changes in the resistance of said cell resulting from the oxidation/reduction of said active electrode caused by temperature changes in said atmosphere to detect a situation in which the free energy of formation of said oxide becomes zero, heating means operable to control the temperature of said cell, and temperature response means responsive when said detection means detects said situation to generate a signal representative of $T_c$, wherein said detection means comprises a wheatstone bridge in which one arm is said cell and another arm of said wheatstone bridge has a resistance intermediate the low and high resistance modes of the cell whereby, when said cell is being cooled at a constant rate from a temperature in excess of $T_c$ towards $T_c$, said wheatstone bridge continuously monitors the resistance of the cell and detects an imbalance caused by a sudden change in the rate of change of the resistance with time, such sudden change being indicative of said situation in which the free energy of formation of said oxide becomes zero, and wherein said heating means does not control the temperature of the said arm of the wheatstone bridge having a resistance intermediate the low and high resistance modes of the cell.

6. Apparatus for determining the partial pressure of oxygen in an atmosphere, comprising a cell having an active electrode which is in use exposed to said atmosphere and a counter electrode separated from the active electrode by a solid electrolyte material having ionic oxygen mobility, said active electrode being composed of a metal exhibiting both positive and negative free energy of formation of an oxide of said metal, said cell operating in the so-called high resistance mode when oxide is present at the active electrode/electrolyte interface and in the so-called low resistance mode when oxide is absent at the active electrode/electrolyte interface, the temperature $T_c$ at which the free energy of formation of said oxide becomes zero being related to the partial pressure of the oxygen in said atmosphere, detection means responsive to changes in the resistance of said cell resulting from the oxidation/reduction of said active electrode caused by temperature changes in said atmosphere to detect a situation in which the free energy of formation of said oxide becomes zero, heating means operable to control the temperature of said cell, and temperature responsive means responsive when said detection means detects said situation to generate a signal representative of $T_c$, wherein said detection means comprises a wheatstone bridge in which one arm is said cell and another arm of said wheatstone bridge has a resistance intermediate the low and high resistance modes of the cell whereby, when said cell is being heated at a constant rate from a temperature below $T_c$ towards $T_c$, said wheatstone bridge continuously monitors the resistance of the cell and detects an imbalance caused by a sudden change in the rate of change of the resistance with time, such sudden change being indicative of said situation in which the free energy of formation of said oxide becomes zero, and wherein said heating means does not control the temperature of the said arm of the wheatstone bridge having a resistance intermediate the low and high resistance modes of the cell.

7. An apparatus according to claim 5 or claim 6, wherein said temperature responsive means comprises a thermo-couple connected to said cell, said thermo-couple being coupled to display means calibrated to convert the signal from said thermo-couple into a direct reading of the partial pressure of oxygen in said atmosphere.

8. An apparatus according to claim 7, wherein said active electrode is composed of palladium.

9. An apparatus according to claim 7, wherein said active electrode is composed of iridium, platinum, ruthenium, or nickel, or alloys thereof.

* * * * *